United States Patent [19]
Schickaneder et al.

[11] Patent Number: 4,764,533
[45] Date of Patent: Aug. 16, 1988

[54] ERYTHRO-1,2-1-PENTANONES

[75] Inventors: Helmut Schickaneder, Eckental-Eckenhaid; Roland Loser, Feldafing, both of Fed. Rep. of Germany

[73] Assignee: Klinge Pharma GmbH, Munich, Fed. Rep. of Germany

[21] Appl. No.: 626,589

[22] Filed: Jul. 2, 1984

Related U.S. Application Data

[63] Continuation of Ser. No. 376,942, May 10, 1982, abandoned.

[30] Foreign Application Priority Data

May 27, 1981 [DE] Fed. Rep. of Germany ....... 3121175

[51] Int. Cl.$^4$ ..................... C07C 93/06; A61K 35/135
[52] U.S. Cl. .................... 514/651; 546/236; 546/237; 548/575; 564/354
[58] Field of Search ............................... 564/354, 324

[56] References Cited

U.S. PATENT DOCUMENTS 3,494,934  2/1970  Wittle ........................... 564/354 X

OTHER PUBLICATIONS

Gopalchari; (I), "Indian Jour. Chem.", vol. 11, pp. 229-233 (1973).
Gopalchari; (II), "Chemical Abstracts", vol. 74, p. 233, Section #40891a (1971).
Leclercq, G. u. Heuson, J. C., Anticancer Research, 1, 217-228 (1981), Drug Interaction with Estrogen Receptors for the . . . ".
Nicholson, R. I. u. Golder, M. P., Europ. J. Cancer, 11, 571-579 (1975), The Effect of Synthetic Anti-oestrogens on the Growth . . . ".
Schnieder, M. et al., Arch. Pharm., 313, 919-925 (1980), Mammatumorhemmende Antiostrogene vom Typ des 3,3'-Dihydroxy . . . ".
Hartmann, R. W., et al., Journal of Medicinal Chemistry, 24, 1192-1197 (1981), "Potential Antiestrogens. Synthesis and . . . ".
Hartmann, R. W., et al., Journal of Medicinal Chemistry, 23, 841-848 (1980), Antiestrogens. Synthesis and Evaluation of . . . ".
Katzenellebogen, B. D., Hormones, Receptors and Breast Cancer, 135-157 (1978), "Basic Mechanisms of Antiestrogen Action".
Hillier, K., Drugs of the Future, V., 564-566 (1980), "U-23,469".
Castaner, J. u. Thorpe, P., Drugs of the Future, III, 211-215 (1978), "Nafoxidine".
Camerman, N. u. Chan, L. Y. Y., Journal of Medicinal Chemistry, 23, 941-945 (1980), "Crystal and Molecular Structure of . . . ".

Primary Examiner—Robert V. Hines
Attorney, Agent, or Firm—Burns, Doane, Swecker & Mathis

[57] ABSTRACT

Erythro-1,2,3-triphenyl-1-pentanones of Formula 1

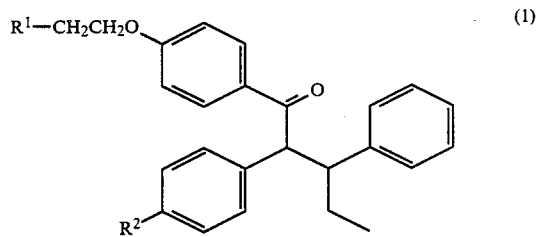

(1)

wherein $R^1$ may be a dimethylamino, diethylamino, piperidin-1-yl- or pyrrolidin-1-yl group and $R^2$ represents a hydrogen atom, a methoxy or hydroxy group, and their pharmacologically acceptable salts, have a pronounced antiestrogenic effect and are suitable for the treatment of hormone-dependent tumors.

They may be prepared by reacting 1,2-diphenyl-ethanone of Formula 2

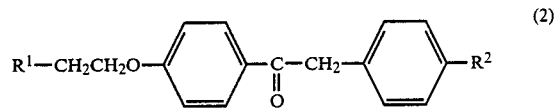

(2)

wherein $R^1$ is as set forth in Formula 1 and $R^2$ represents a hydrogen atom or a methoxy group, with sodium hydride in anhydrous dimethyl-formamide, isolating after conversion with 1-chloro-1-phenylpropane, the erythro form from the reaction product and possibly releasing the hydroxy group from the methoxy group by selective cleavage with hydrobromic acid.

9 Claims, No Drawings

ERYTHRO-1,2-1-PENTANONES

This is a continuation of application Ser. No. 376,942, filed May 10, 1982 and now abandoned.

BACKGROUND OF THE INVENTION

The invention concerns 1,2,3-triphenyl-1-pentanone derivatives which are effective in treating estrogen-dependent tumors.

It is disclosed in British Pat. No. 1 013 907 that 1,1,2-triphenylalkene derivatives may possess antiestrogenic properties and are thus suitable for the treatment of hormone-dependent tumors. In addition to these compounds, a series of further nonsteroid, antiestrogenic active ingredients has become known, the basic structures of which are of the triarylalkene type.

It is an object of this invention to provide new and effective compounds exhibiting high antiestrogenic activity which are thus useful in the treatment of estrogen-dependent tumors.

It is a further object of this invention to provide a compound having high binding affinity to the estradiol receptor of the uterus.

SUMMARY OF THE INVENTION

It has now been found surprisingly that antiestrogenically effective compounds are also present in the heretofore unknown class of the 1,2,3-triphenyl-1-pentanones of formula 1.

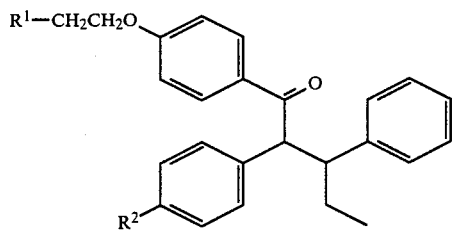

wherein $R^1$ may be a dimethylamino, diethylamino, pyrrolidin-1-yl or a piperidin-1-yl group, and $R^2$ represents a hydrogen atom, a methoxy or a hydroxy group. Also effective are their pharmacologically acceptable salts.

As shall be shown hereinafter, the compounds claimed have a high bonding affinity, in their erythro form, to the estrogen receptor. Based on their high specific activity, the compounds claimed exhibit a pronounced autiuterotropic activity, which is of decisive importance for any mammatumor inhibiting activity.

The invention further concerns a process for the preparation of compounds of the general formula 1, wherein 1,2-diphenylethanones of the general formula 2

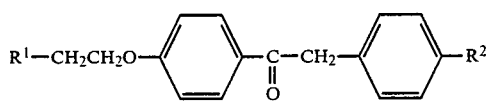

wherein $R^1$ is defined as in general formula 1 and $R^2$ is a hydrogen atom or a methoxy group, are reacted in anhydrous dimethylformamide with sodium hydride to form a mixture of the erythro and threo forms of the 1,2,3-triphenyl-1-pentanone. The erythro form is isolated by means of crystallization after reaction with 1-chloro-1-phenylpropane. Compounds of the general formula 1, wherein $R^2$ is a hydroxy group, are obtained by subjecting the methoxy-substituted compounds of the general formula 1 to a selective methylether cleavage.

DETAILED DESCRIPTION OF THE INVENTION 1,2-diphenylethanones may be prepared in the following manner.

Compounds of the general formula 3

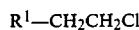

wherein $R^1$ may be a dimethylamino, diethylamino, pyrrolidin-1-yl or a piperidin-1-yl group, are converted in the presence of alkali with phenol to ethers of the general formula 4

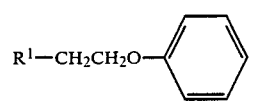

wherein $R^1$ is as defined above. Compounds of the general formula 4 may be converted, in a Friedel-Crafts reaction with phenylacetic acid chlorides of the general formula 5

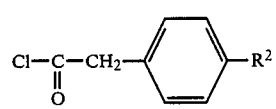

wherein $R^2$ represents a hydrogen atom or a methoxy group, into the 1,2-diphenylethanones of the general formula 2. Following the action of sodium hydride on compounds of general formula 2 and subsequent conversion with 1-chloro-1-phenylpropane, compounds of general formula 1 are obtained, wherein $R^2$ represents a hydrogen atom or a methoxy group.

Crystallization from dilute methanol yields the compounds in their pure erythro form.

When the methoxy derivatives of general formula 1 are heated under reflux with a solution of hydrobromic acid, they are cleaved into compounds of general formula 1, wherein $R^2$ represents a hydroxy group.

The following compounds are exemplary of the 1,2,3-triphenyl-1-pentanone compounds claimed:

TABLE 1

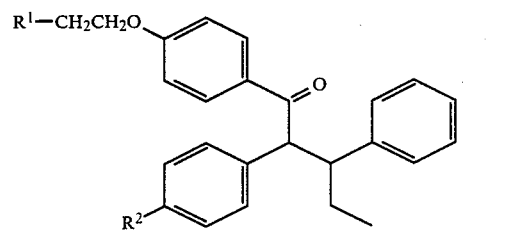

| No. of Compound | $R^1$ | $R^2$ | Melting Point |
|---|---|---|---|
| 1 | $(CH_3)_2N$ | H | 129–131° C. |
| 2 | $(C_2H_5)_2N$ | H | 108–109° C. |

TABLE 1-continued

R¹—CH₂CH₂O—[structure with carbonyl and phenyl groups]—R²

| No. of Compound | R¹ | R² | Melting Point |
|---|---|---|---|
| 3 | pyrrolidinyl (N in 5-ring) | H | 128° C. |
| 4 | piperidinyl (N in 6-ring) | H | 125° C. |
| 5 | (CH₃)₂N | OCH₃ | 88–89° C. |
| 6 | (CH₂H₅)₂N | OCH₃ | 89–90° C. |
| 7 | pyrrolidinyl (N in 5-ring) | OCH₃ | 96–98° C. |
| 8 | piperidinyl (N in 6-ring) | OCH₃ | 98–99° C. |
| 9 | (CH₃)₂N | OH | 200° C. |
| 10 | pyrrolidinyl (N in 5-ring) | OH | 181–182° C. |

The erythro and threo forms of 1,2,3-triphenyl-1-pentanone derivatives of general formula 1 are clearly different in their proton resonance signals of methyl protons in the pentanone chain. The signals of the erythro form are shifted to the high field in relation to the threo form, which has also been found with hexestrol derivatives. (R. Gaswami, S. G. Harsy, D. F. Heiman and J. A. Katzenellenbogen, J. Med. Chem. 23, 1002 (1980)).

A high antiestrogenic activity of the erythro forms of the 1,2,3-triphenyl-1-pentanone derivatives of general formula 1 was determined. They are thus therapeutically useful in the treatment of estrogen-dependent tumors.

The determination of the binding affinity to the estradiol receptor was effected by means of the rabbit uterus cytosol. The compounds claimed exhibit high bonding affinities.

The measurement of the antiuterotropic action was effected following a three-week treatment with the active ingredient of sexually mature, female rats. The compounds claimed exhibit pronounced antiuterotropic effects.

The tumor inhibiting action was measured following a four-week treatment with the active ingredient on female rats, with mammatumors induced previously with 7,12-dimethylbenz(a)anthracene. The compounds exhibit a strong inhibition of the growth of tumors.

The compounds of the invention thus represent a valuable addition to the range of available medicines and may be employed in the treatment of malignant mammatumors.

The invention further includes medicines containing a compound of general formula 1 as the active ingredient, in addition to the usual pharmaceutical carriers and auxiliary substances.

The compounds are preferably administered orally. The daily oral dosage is usually from about 0.01 to about 0.2 g, preferably 0.02 to 0.1 g. However, it may be necessary in certain cases to deviate from the above cited doses, as a function of individual response to the drug or the manner of its formulation and the frequency at which the drug is administered. Thus, in certain cases it may be sufficient to administer less than the aforementioned minimum dosage, while in other cases the aforementioned upper limit must be exceeded. When larger amounts are administered, it may be advantageous to divide them over a day in several smaller, individual doses. The active ingredients may be compounded prior to oral administration, for example in capsules, tablets or as dragees.

The drugs may be processed into tablets or dragees cores by mixing the active ingredient with solid, powdered carrier substances, such as micronized cellulose, potato or corn starch, with additions such as sodium citrate, calcium carbonate and binders such as polyvinyl pyrrolidone, gelatin or cellulose derivatives, possibly with the addition of lubricants such as magnesium stearate, sodium lauryl sulfate or polyethylene glycols. For oral administration, they may be mixed with flavor enhancers.

Other suitable forms for administration of the drug are coated capsules, for example of hard gelatin, or sealed soft gelatin capsules with a plasticizer, such as glycerine. The coated capsules contain the active ingredient preferably in the form of granulates, and may be mixed with fillers, such as potato starch or amylopectin, cellulose derivatives or highly dispersed silica. In soft gelatin capsules the active ingredient is dissolved or suspended preferably in suitable liquids, for example in vegetable oil or liquid polyethylene glycols.

The invention shall become more apparent from the examples which follow. These examples are given with the understanding that they are intended to illustrate the invention but are not intended to act as a limitation on the scope of the present invention.

EXAMPLE 1

1-(4'-(2-dimethylaminoethoxy)-phenyl)-2,3-diphenyl-1-pentanone

Preparation of Starting Materials (a) Preparation of 1-(4'-(2-dimethylaminoethoxy)-phenyl-2-phenyl)-1-ethanone 20.2 g (0.1 mole) N,N-dimethyl-2-phenoxyethylaminohydrochloride and 15.5 g (0.1 mole) phenylacetic acid chloride are suspended in 350 ml anhydrous methylene chloride and reacted at room temperature with 26.7 g (0.2 mole) anhydrous aluminum chloride in portions. After the addition is completed, the reaction solution is heated for one hour to reflux temperature, then poured on ice and made alkaline with 25% sodium hydroxide. The organic phase is separated, washed to attain a neutral pH, and dried over sodium sulfate. The solvent is removed by vacuum and the residue crystallized from petroleum ether. Colorless crystals with a melting point of 54° to 55° C. were obtained in a yield of 17.0 g (60%); $R_f=(0.25$ HCCL$_3$/MeOH(95/5)).

$C_{18}H_{21}NO_2$ (283.4)

$^1$H-NMR-spectrum (CDCl$_3$)[1]: 2.33 s (6) N(CH$_3$)$_2$; 2.73 t (2) CH$_2$-N (J=6.0); 4.10 t (2) OCH$_2$ (J=6.0); 4.20 s (2) CH$_2$; 6.93 d (2) aromatic-H (J=9.0); 7.28 s (5) aromatic-H; 8.00 d (2) aromatic-H (J=9.0).

[1] Recorded at 60 MHz; the chemical shifts are given in ppm against TSM (δ=0,0), relative intensities are added in parentheses. s=singlets; d=doublets; t=triplets; m=multiplets. J=coupling constant in Hz.

(b) Preparation of 1-chloro-1-phenylpropane 13.6 g (0.1 mole) of 1-phenylpropan-1-ol are taken up in petroleum ether and are reacted at −20° C. with hydrochloric acid until the precipitation of water is terminated. Subsequently, the organic phase is washed neutral with water, dried (sodium sulfate) and the petroleum ether removed in a vacuum. The bright yellow, thermolabile oil is used without further purification. The oil has an R$_f$ of 0.8 (CH$_2$Cl$_2$) and is attained in a yield of 13.1 g (85%).

$C_9H_{11}Cl$ (154.67)

$^1$H-NMR spectrum (CDCl$_3$): 0.97 t (3) CH$_3$ (J=7.0); 1.73 to 2.40 m (2) CH$_2$; 4.77 t (1) CH (J=7.6); 7.35 s (5) aromatic H.

Preparation of a compound of the present invention (c) erythro-1-(4'-(2-dimethylaminoethoxy)-phenyl)-2,3-diphenyl-1-pentanone To a suspension of 150 ml anhydrous dimethylformamide and 2.4 g (0.1 mole) sodium hydride, a solution of 28.3 g (0.1 mole) 1-(4'-(2-dimethylaminoethoxy)-phenyl)-2-phenyl-1-ethanone in 150 ml anhydrous dimethylformamide is added slowly, in drops, at 20° C. and under N$_2$ atmosphere. Following the completion of the addition, the mixture is allowed to react for one-half hour at room temperature and then a solution of 18.5 g (0.12 mole) 1-chloro-1-phenylpropane in 50 ml anhydrous dimethylformamide is added in drops, at room temperature. After 2 hours the reaction solution is quenched with water and taken up in ethylacetate. The organic phase is washed with water to obtain a neutral pH, dried over sodium sulfate, and condensed in a vacuum. The erythro form may be crystallized out of a methanol/water solution. Colorless crystals with melting points of 129° to 131° C. and R$_f$=0.3 (CHCl$_3$/MeOH (9/1)) are obtained in a yield of 18.0 g (45%).

$C_{27}H_{31}No_2$ (401.6) Calculated: C 80.76, H 7.78, N 3.49. Determined: C 80.93, H 7.88, N 3.46.

Molecular weight: 401 (determined by mass spectrometry).

IR spectrum (KBr): ν (C=O) 1665 cm$^{-1}$.

$^1$H-NMR spectrum (CDCl$_3$): 0.57 t (3) CH$_3$ (J=6.0); 1.10 to 1.77 m (2) CH$_2$; 2.28 s (6) N(CH$_3$)$_2$; 2.67 t (2) CH$_2$-N (J=5.0); 3.17 to 3.80 m (1) CH; 4.00 t (2) OCH$_2$ (J=5.0); 4.90 d (1) CH—C=O (J=11.8); 6.80 d (2) aromatic H (J=9.0); 7.00 to 7.63 m (10) aromatic H; 7.80 d (2) aromatic-H (J=9.0).

(d) Preparation of erythro-1-(4'-(2-dimethylaminoethoxy)-phenyl)-2,3-diphenyl-1-pentanone hydrochloride Hydrochloric acid is passed under cooling with ice into a solution of 40.1 g erythro-1-(4'-2-dimethylaminoethoxy)-phenyl)-2,3-diphenyl-1-pentanone in 250 ml ether, until the ether solution clearly reacts in an acidic manner. The hydrochloride precipitated is suctioned off and dried. Colorless crystals with a melting point of 190°–191° C. are recovered; yield is quantitative.

(e) Preparation of threo-1-(4'-(2-dimethylaminoethoxy)-phenyl)-2,3-diphenyl-1-pentanone The mother liquor of the crystallizate of Example 1c is purified by column chromatography (silica gel; solvent: CHCl$_3$/MeOH (9/1)). The threo form is thereby obtained as a colorless oil with a slight yield (R$_f$=0.3 (CHCl$_3$/MeOH) (9/1); yield: 1.6 g (4%)).

$^1$H-NMR spectrum (CDCl$_3$): 0.72 t (3) CH$_3$ (J=6.4); 1.10 to 2.00 m (2) CH$_2$; 2.30 s (6) N(CH$_3$)$_2$; 2.73 t (2) CH$_2$-N (J=5.0); 3.20 to 3.80 m (1) CH; 4.07 to (2) OCH$_2$ (J=5.0); 4.73 d (1) CH—C=O (J=10.6); 6.63 to 8.20 m (14) aromatic H.

EXAMPLE 2

Preparation of erythro-1-(4'-(2-diethylaminoethoxy)-phenyl)-2,3-diphenyl-1-pentanone 31.1 g (0.1 mole) of 1-(4'-(2-diethylaminoethoxy)-phenyl)-2-phenyl-1-ethanone (melting point 35°–36° C., from petroleum ether) prepared in a manner similar to Example 1(a), are reacted as described in Example 1(c). Colorless crystals with a melting point of 108°–109° C. (petroleum ether) result; yield 6.0 g (14%); R$_f$=0.3 (CHCl$_3$/MeOH (9/1));

$C_{29}H_{35}NO_2$ (429.6) Calculated: C 81.08 H 8.21 N 3.26. Determined: C 80.96 H 8.15 N 3.20.

Molecular weight: 429 (determined by mass spectrometry).

IR spectrum (KBr) ν (C=O) 1670 cm$^1$.

$^1$H-NMR spectrum (CDCl$_3$): 0.57 t (3) CH$_3$ (J=6.0); 1.03 t (6) CH$_3$ (J=7.0); 1.10 to 1.73 m (2) CH$_2$; 2.60 q (4) CH$_2$ (J=7.0); 2.80 t (2) CH-N (J=5.2); 3.13 to 3.77 m (1) CH; 4.00 t (2) OCH$_2$ (J=5.2); 4.87 d (1) CH—C=O (J=11.8); 6.80 d (2) aromatic H (J=9.0); 7.00 to 7.60 m (10) aromatic H; 7.80 d (2) aromatic H (J=9.0).

EXAMPLE 3

Preparation of erythro-2,3-diphenyl-1-(4'-(2-pyrrolidin-1-yl-ethoxy)-phenyl)-1-pentanone 30.9 g (0.1 mole) 2-phenyl-1-(4'-(2-pyrrolidin-1-yl-ethoxy)-phenyl)-1-ethanone (melting point 77° to 78° C. from petroleum ether) are prepared in a manner similar to Example 1(a), and reacted as described in Example 1(c). Colorless crystals with a melting point of 128° C. (ether) result; yield: 12.8 g (30%).

R$_f$=0.35 (CHCl$_3$/MeOH) (9/1).

$C_{29}H_{33}NO_2$ (427.6) Calculated: C 81.46 H 7.78 N 3.28. Determined: C 81.32 H 7.80 N 3.17.

Molecular weight: 427 (determined by mass spectrometry).

IR spectrum (KBr): ν (C=O) 1669 cm$^{-1}$.

$^1$H-NMR spectrum (CDCl$_3$): 0.57 t (3) CH$_3$ (J=6.0); 1.13 to 1.73 m (2) CH$_2$; 1.77 to 1.97 m (4) CH$_2$; 2.37 to 2.73 m (4) CH$_2$; 2.87 t (2) CH$_2$ (J=5.2); 3.20 to 3.77 m (1) CH; 4.03 t (2) OCH$_2$ (J=5.2); 4.90 d (1) CH—C=O (J=11.8); 6.80 d (2) aromatic H (J=9.0); 7.00 to 7.57 m (10) aromatic H; 7.80 d (2) aromatic H (J=9.0).

EXAMPLE 4

Preparation of erythro-2,3-diphenyl-1-(4'-(2-piperidin-1-yl-ethoxy)-phenyl)-1-pentanone 32.3 g (0.1 mole) 2-phenyl-1-(4'-2-piperidin-1-yl-ethoxy)-phenyl)-1-ethanone (melting point 73° C. from petroleum ether), prepared in a manner similar to Example 1(a), are reacted as described in Example 1(c). Colorless crystals with a melting point of 125° C. (petroleum ether) result; yield=40%. $R_f$=0.60 (CHCl$_3$/MeOH (7/3)).

$C_{30}H_{35}NO_2$ (441.6) Calculated: C 81.59 H 7.99 N 3.17. Determined: C 81.47 H 7.87 N 3.05.

Molecular weight: 441 (determined by mass spectrometry).

IR spectrum (KBr): $\nu$ (C=O) 1669 l cm$^{-1}$.

$^1$H-NMR spectrum (CDCl$_3$): 0.57 t (3) CH$_3$ (J=6.0); 1.10 to 1.83 m (8) CH$_2$; 2.30 to 2.70 m (4) CH$_2$; 2.73 t (2) CH$_2$-N (J=5.2); 3.17 to 3.73 m (1) CH; 4.07 t (2) OCH$_2$ (J=5.2); 4.87 d (1) CH—C=O (J=11.8); 6.73 d (2) aromatic H (J=9.0); 6.90 to 7.57 m (10) aromatic H; 7.77 d (2) aromatic H (J=9.0).

EXAMPLE 5

Preparation of erythro-1-(4'-(2-dimethylaminoethoxy)-phenyl)-2-(4'-methoxyphenyl)-3-phenyl-1-pentanone 31.3 g (0.1 mole) 1-(4'-(2-dimethylaminoethoxy)-phenyl)-2-(4'-methoxyphenyl)-1-ethanone (melting point 75° to 77° C. from petroleum ether), prepared in a manner similar to Example 1(a) from 20.2 g (0.1 mole) N,N-dimethyl-2-phenoxyethylamine hydrochloride and 18.5 g (0.1 mole) 4-methoxyphenylacetic acid chloride, are reacted as described in Example 1(c). Colorless crystals with a melting point of 88° to 89° C. (petroleum ether) are recovered in a yield of 5.6 g (13%). $R_f$=0.25 (CHCl$_3$/MeOH (9/1)).

$C_{28}H_{33}NO_3$ (431.6) Calculated: C 77.93 H 7.71 N 3.25. Determined: C 77.92 H 7.65 N 3.18.

Molecular weight: 431 (determined by mass spectrometry).

IR spectrum (KBr): $\nu$ (C=O) 1165 cm$^{-1}$.

$^1$H-NMR spectrum (d$_6$-acetone): 0.58 t (3) CH$_3$ (J=6.0); 1.10 to 1.73 m (2) CH$_2$; 2.20 s (6) N(CH$_3$)$_2$; 2.60 t (2) CH$_2$—N (J=5.6); 3.13 to 3.73 m (1) CH; 3.74 s (3) OCH$_3$; 4.07 t (2) OCH$_2$ (J=5.6); 5.20 d (1) CH—C=O (J=11.6); 6.70 to 8.13 m (13) aromatic H.

EXAMPLE 6

Preparation of erythro-1-(4'-(2-diethylaminoethoxy)-phenyl)-2-(4'-methoxyphenyl)-3-phenyl-1-pentanone 34.1 g of 1-(4'-(2-diethylaminoethoxy)-phenyl)-2-(4'-methoxyphenyl)-1-ethanone (melting point 52° to 53° C., from petroleum ether), prepared in a manner similar to Example 1(a) and Example 5, are reacted as described in Example 1(c). Colorless crystals with a melting point of 89°-90° C. (methanol/water) are recovered; $R_f$0.35 (CHCl$_3$/MeOH)); yield: 3.2 g (7%).

$C_{30}H_{37}NO_3$ (459.6) Calculated: C 78.40 H 8.11 N 3.05. Determined: C 78.22 H 8.07 N 2.92.

Molecular weight: 459 (determined by mass spectrometry).

IR spectrum (KBr): $\nu$ (C=O) 1660 cm$^{-1}$.

$^1$H-NMR spectrum (CDCl$_3$): 0.57 t (3) CH$_3$ (J=6.2); 1.00 t (6) CH$_3$ (J=7.0); 1.13 to 1.73 m (20 CH$_2$; 2.57 q (4) CH$_2$ (J=7.0); 2.77 t (2) CH$_2$—N (J=5.0); 3.03 to 3.67 m (1) CH; 3.73 s (3) OCH$_3$; 3.97 t (2) OCH$_2$ (J=5.0); 4.77 d (1) CH—C=O (J=11.8); 6.53 to 7.90 m (13) aromatic H.

EXAMPLE 7

Preparation of erythro-2-(4'-methoxyphenyl)-3-phenyl-1-(4'-(2-pyrrolidin-1-yl-ethoxy)-phenyl)-1-pentanone 33.9 g (0.1 mole) 2-(4'-methoxyphenyl)-1-(4'-2-pyrrolidin-1-yl-ethoxy)-phenyl)-1-ethanone (melting point 71°-72° C., from petroleum ether) prepared in a manner similar to Example 1(a) and Example 5, are reacted as in Example 1(c). Colorless crystals with a melting point of 96°-98° C. (petroleum ether/ether) are recovered in a yield of 11.9 g (26%). $R_f$0.25 (CHCl$_3$/MeOH (9/1)).

$C_{30}H_{35}NO_3$ (457.6) Calculated: C 78.74 H 7.71 N 3.06. Determined: C 78.89 H 7.69 N 3.15.

Molecular weight: 431 (determined by mass spectrometry).

IR spectrum (KBr): $\nu$ (C=O) 1669 cm$^{-1}$.

$^1$H-NMR spectrum (CDCl$_3$): 0.6 t (3) CH$_3$ (J=6.0); 1.10 to 1.73 m (2) CH$_2$; 1.60 to 2.00 m (4) CH$_2$; 2.37 to 2.73 m (4) CH$_2$; 2.87 t (2) CH—N (J=5.4); 3.10 to 3.73 m (1) CH; 3.80 s (3) OCH$_3$; 4.07 t (2) OCH$_2$ (J=5.4); 4.83 d (1) CH—C=O (J=11.8); 6.63 to 7.97 m (13) aromatic H.

EXAMPLE 8

Preparation of erythro-2-(4'-methoxyphenyl)-3-phenyl-1-(4'-(2-piperidin-1-yl-ethoxy)-phenyl)-1-pentanone 35.3 g (0.1 mole) 2-(4'-methoxyphenyl)-1-(4'-2-piperidin-1-yl-ethoxy)-phenyl)-1-ethanone (melting point 81° C. from ethanol) prepared in a manner similar to Example 1(a) and Example 5, are reacted as described in Example 1(c). Colorless crystals with a melting point of 98° to 99° C. (petroleum ether/ether) are recovered; yield: 7.5 g (16%); $R_f$(CHCl$_3$/MeOH (9/1)).

$C_{31}H_{37}NO_3$ (471.6).

Molecular weight: 471 (determined by mass spectrometry).

IR spectrum (Br): $\nu$ (C=O) 1667 cm$^{-1}$.

$^1$H-NMR spectrum (CDCl$_3$): 0.58 t (3) CH$_3$ (H=6.2); 1.10 to 1.77 m (8) CH$_2$; 2.27 to 2.60 m (4) CH$_2$; 2.70 t (2) CH$_2$—N (J=5.4); 3.07 to 3.73 m (1) CH; 3.75 s (3) OCH$_3$; 4.07 t (2) OCH$_2$ (J=5.4); 4.83 d (1) OHC=O (J=11.8); 6.57 to 7.93 m (13) aromatic H.

EXAMPLE 9

Preparation of erythro-1-(4'-(2-dimethylaminoethoxy)-phenyl)-2-(4'-hydroxyphenyl)-3-phenyl-1-pentanone 43.2 g (0.1 mole) erythro-1-(4'-2-dimethylaminoethoxy)-phenyl)-2-(4'-methoxyphenyl)-3-phenyl-1-pentanone were heated with 400 ml 48% aqueous solution of hydrobromic acid for 2 hours under reflux. Subsequently, the solution is condensed to dryness under vacuum, the residue made basic with approximately 200 ml of a dilute aqueous ammonia solution and extracted three times with 100 ml aliquots of ethylacetate. The organic phase is washed with water to neutral pH and the solvent removed after drying over sodium sulfate. The residue is crystallized from methanol several times. Colorless crystals with a melting point of 200° C. are recovered in a yield of 2.46 g (59%); $R_f=0.20$ (CHCl$_3$/CH$_3$OH (7/3)).

C$_{27}$H$_{31}$NO$_3$ (417.5) Calculated: C 77.67 H 7.48 N 3.35. Determined: C 77.66 H 7.51 N 3.23.

Molecular weight: 417 (determined by mass spectrometry).

IR spectrum (KBr): $\nu$ (O—H) 3600 to 3100 cm$^{-1}$. $\nu$ (C=O) 1670 cm$^{-1}$.

$^1$H-NMR spectrum (d$_6$-acetone): 0.57 t (3) C$\underline{H}_3$ (J=6.0); 1.17 to 1.67 m (2) C$\underline{H}_2$; 2.20 s (6) N(C$\underline{H}_3$)$_2$; 2.63 t (2) C$\underline{H}_2$N (J=5.0); 2.83 to 3.67 m (1) C$\underline{H}$ (J=5.0); 4.10 t (2) OC$\underline{H}_2$ (J=5.0); 5.17 d (1) C$\underline{H}$—C=O (J=11.8); 6.67 to 8.17 m (13) aromatic H.

EXAMPLE 10

Preparation of erythro-2-(4'-hydroxyphenyl)-3-phenyl-1-(4'-(2-pyrrolidin-1-yl-ethoxy)-phenyl)-1-pentanone 45.7 g (0.1 mole) erythro-2-(4'-methoxyphenyl)-3-phenyl-1-(4'-(2-pyrrolidin-1-yl-ethoxy)-phenyl)-1-pentanone are subjected in a manner similar to Example 9 to a partial ether cleavage and processed accordingly. Colorless crystals with a melting point of 181°–182° C. (methanol) are recovered; yield: 18.1 g (41%). $R_f=0.35$ (CHCl$_3$/CH$_3$OH (7/3)).

C$_{29}$H$_{33}$NO$_3$ (443.6).

Molecular weight: 443 (determined by mass spectrometry).

IR spectrum (KBr): $\nu$ (O—H) 3600 to 3100 cm$^{-1}$. $\nu$ (C=O) 1669 cm$^{-1}$.

$^1$H-NMR spectrum (CDCl$_3$/d$_6$-DMSO (4/1)): 0.57 t (3) C$\underline{H}_3$ (J=6.0); 1.17 to 1.93 m (2) C$\underline{H}_2$; 1.77 m (4) C$\underline{H}_2$; 2.57 m (4) CH$_2$NCH$_2$; 2.83 t (2) C$\underline{H}_2$ (J=5.0); 3.07 to 3.60 m (1) C$\underline{H}$; 4.07 t (2) OC$\underline{H}_2$ (J=5.0); 4.83 d (1) C$\underline{H}$—C=O (J=11.8); 6.57 to 7.90 m (13) aromatic H; 8.77 wide (1) O$\underline{H}$ (interchangeable with D$_2$O).

EXAMPLE 11

Preparation of erythro-2-(4'-methoxyphenyl)-3-phenyl-1-(4'-(2-pyrrolidin-1-yl-ethoxy)-phenyl)-1-pentanone containing medicine 20 g of a powdered active ingredient are mixed with 40 g lactose and 140 g starch, and subsequently intermixed with 33 g talcum and 13 g calcium stearate. After careful mixing, the composition is filled into 2000 hard gelatine capsules of a suitable size, each capsule containing 10 mg of the active ingredient.

EXAMPLE 12

Preparation of erythro-1-(4'-(2-dimethylaminoethoxy)-phenyl)-2-(4'-hydroxyphenyl)-3-phenyl-1-pentanone containing medicine 20 g of a finely powdered active ingredient are mixed with 111 g mannitol, 15 g corn starch, and 6 g alginic acid and granulated. The dried granulate is mixed carefully with 0.75 g methyl cellulose and 1.5 g magnesium stearate, and pressed into 1000 tablets, so that each tablet contains 20 mg of the active ingredient.

Pharmacological Investigations (a) Bonding affinity to the estradiol receptor The measurement of the bonding affinity to the estradiol receptor was affected by the method of N. Devleeschouwer, G. Leclercq, A. Danguy and J. C. Heuson, (Europ. J. Cancer, 14, 721–723 (1978)). The uterus cytosal of female, prepubertal, white rabbits (New Zealand) weighing 2 kg, was incubated for 18 hours at 40° C. with 2.5×10$^{-9}$M ($^3$H) estradiol, with the further addition of unmarked estradiol (control) or the test substance in different concentrations. The bonding affinity to the estradiol receptor is expressed by the concentration of unmarked estradiol (control) or the test substance added to the uterus cytosol, which effects a 50% displacement of the ($^3$H) estradiol bound to the estradiol receptor.

TABLE 2

Bonding Affinity of Test Substances $$R^1\text{—CH}_2\text{CH}_2\text{O—}\underset{R^2}{\phantom{X}}\text{(structure as shown)}$$

| No. of Compound | R$^1$ | R$^2$ | ED$_{50}$* (M) |
|---|---|---|---|
| Estradiol (control) | — | — | 1.3 × 10$^{-9}$ |
| 1 | (CH$_3$)$_2$N | H | 6.0 × 10$^{-6}$ |
| 2 | (C$_2$H$_5$)$_2$N | H | 4.0 × 10$^{-6}$ |
| 3 | pyrrolidin-1-yl | H | 6.0 × 10$^{-6}$ |
| 4 | piperidin-1-yl | H | 2.8 × 10$^{-6}$ |
| 5 | (CH$_3$)$_2$N | OCH$_3$ | 4.5 × 10$^{-6}$ |
| 6 | (C$_2$H$_5$)$_2$N | OCH$_3$ | 5.0 × 10$^{-7}$ |
| 7 | pyrrolidin-1-yl | OCH$_3$ | 1.1 × 10$^{-6}$ |
| 8 | piperidin-1-yl | OCH$_3$ | 1.2 × 10$^{-9}$ |
| 9 | (CH$_3$)$_2$N | OH | 5.4 × 10$^{-9}$ |
| 10 | pyrrolidin-1-yl | OH | 8.0 × 10$^{-8}$ |

*Concentration of substance displacing 50% ($^3$H) estradiol from the estradiol receptor.

(b) Antiuterotropic Effect

The antiuterotropic effect was determined by a modified Dorfman test (R. I. Dorfman, "Methods in Hormone Research II" p. 707, Academic Press, New York-London, 1962), on sexually mature female Sprague-Dawley rats.

The test compounds were taken up in a 0.25% aqueous agar suspension and administered by esophageal tube over a period of 21 days, six times per week. Following the completion of the experiment, the uterus weight of animals treated with the active ingredient was related to the uterus weight of the control animals, which received only an empty agar suspension.

TABLE 3
Antiuterotropic Activity of Test Substances

| Compound No. | No. of experimental animals | Dose mg/kg/day | Weight of uterus compared to control animals |
|---|---|---|---|
| 2 | 10 | 3 | −54% |
| 3 | 10 | 3 | −36% |
| 4 | 10 | 3 | −28% |
| 5 | 10 | 3 | −47% |
| 7 | 10 | 3 | −43% |
| 9 | 10 | 3 | −54% |

(c) Mammatumor Inhibiting Effect

The tumor inhibiting effect was determined on the model of mammatumors induced by means of 7,12-dimethylbenz(a)anthracene of female Spraque-Dawley rats (Hannover strain), by the method of M. J. Golder (Europ. J. Cancer 11, 571 (1975)) and D. P. Griswold et al. (Cancer Research 26, 2169 (1966)).

The test substance were taken up in a 0.25% agar solution and administered by esophageal tube over a period of 28 days, six times per week. Twice weekly and on the 28th day of the experiment, the number of animals was ascertained and the tumor surface (mm²/animal) of the therapy and control animals measured. At the completion of the experiment, the percentage increase of the average tumor surface of the treated animals was determined, compared with the control animals, which were valued at 100%.

TABLE 4
Tumor Inhibiting Effect of Test Substances

| No. of Compound | Number of experimental animals | Dose mg/kg/day | Relative Increase of average tumor surface |
|---|---|---|---|
| Empty control | 10 | — | 100% |
| 1 | 10 | 3 | 53% |
| 9 | 10 | 3 | 30% |

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. An erythro-1,2,3-triphenyl-1-pentanone compound having the formula:

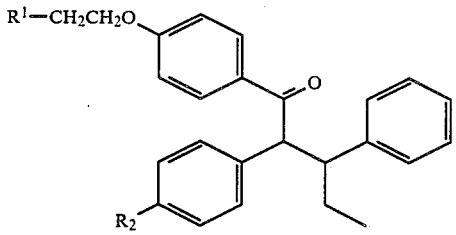

wherein $R^1$ is a dimethylamino group, and $R^2$ is a hydroxy group, and its pharmacologically acceptable salts.

2. A pharmaceutical composition comprising a compound as claimed in claim 1 in a pharmacologically acceptable carrier.

3. The composition of claim 2 wherein said composition is adapted for oral use.

4. The composition of claim 3 in tablet, capsule, or dragee form.

5. The composition of claim 3 in the form of a suspension.

6. The composition of claim 3, in dosage unit form in which each dosage unit contains a tumor inhibiting effective amount of said compound.

7. The composition of claim 6, in dosage unit form in which each dosage unit contains from about 0.01 to about 0.2 g of said compound.

8. The composition of claim 7, in which each dosage unit contains about 0.02 to about 0.1 g of said compound.

9. A method of inhibiting hormone-dependent tumors which comprises the step of administering a tumor-inhibiting effective amount of a compound as claimed in claim 1.

* * * * *